United States Patent
Shechter et al.

(10) Patent No.: US 6,726,838 B2
(45) Date of Patent: *Apr. 27, 2004

(54) BIOFILM CARRIER, METHOD OF MANUFACTURE THEREOF AND WASTE WATER TREATMENT SYSTEM EMPLOYING BIOFILM CARRIER

(75) Inventors: Ronen Itzhak Shechter, Ramat Tivon (IL); Eytan B Levy, Rosh Ha'ayn (IL)

(73) Assignee: Agwise Wise Water Technologies Ltd., Netanya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/041,524

(22) Filed: Jan. 7, 2002

(65) Prior Publication Data

US 2003/0127378 A1 Jul. 10, 2003

(51) Int. Cl.$^7$ .................................................. C02F 3/06
(52) U.S. Cl. ........................ 210/150; 210/197; 210/220; 210/616; 210/629
(58) Field of Search ........................ 210/150, 151, 210/194, 197, 220, 615, 616, 617, 629

(56) References Cited

U.S. PATENT DOCUMENTS

| | | |
|---|---|---|
| 1,790,975 A | 2/1931 | Dallas et al. |
| 3,133,017 A | 5/1964 | Lambeth |
| 3,957,931 A * | 5/1976 | Ellis et al. ............... 210/150 |
| 4,179,366 A | 12/1979 | Kaelin |
| 4,188,289 A | 2/1980 | Besik |
| 4,333,893 A | 6/1982 | Clyde ......................... 261/94 |
| 4,385,988 A | 5/1983 | Hypponen ................ 210/150 |
| 4,522,767 A | 6/1985 | Billet et al. ................. 261/94 |
| 4,537,731 A | 8/1985 | Billet et al. ................. 261/94 |
| 4,810,377 A | 3/1989 | Kato et al. |
| 4,814,085 A | 3/1989 | Fujii et al. .................... 264/44 |
| 4,814,125 A | 3/1989 | Fujii et al. ............... 210/510.1 |
| 4,842,920 A | 6/1989 | Banai et al. ................ 428/184 |
| 4,985,182 A | 1/1991 | Basse et al. ................. 261/94 |
| 4,999,103 A | 3/1991 | Bogart ........................ 210/151 |
| 5,080,793 A | 1/1992 | Urlings ........................ 210/150 |
| 5,168,058 A | 12/1992 | Bohak et al. ............ 435/240.23 |
| 5,192,442 A | 3/1993 | Piccirillo et al. ............ 210/616 |
| 5,200,081 A * | 4/1993 | Stuth ........................... 210/197 |
| 5,217,616 A | 6/1993 | Sanyal et al. ............... 210/617 |
| 5,429,740 A * | 7/1995 | Van Der Herberg ........ 210/151 |
| 5,458,779 A | 10/1995 | Odegaard .................... 210/616 |
| 5,486,292 A | 1/1996 | Bair et al. .................... 210/616 |
| 5,543,039 A | 8/1996 | Odegaard .................... 210/150 |
| 5,558,763 A * | 9/1996 | Funakoshi et al. .......... 210/150 |
| 5,779,886 A * | 7/1998 | Couture ....................... 210/150 |
| 5,783,066 A | 7/1998 | Aylmore ...................... 210/150 |
| 5,783,069 A | 7/1998 | Frank .......................... 210/150 |
| 5,871,674 A | 2/1999 | Leva ............................ 261/94 |
| 5,902,484 A | 5/1999 | Timpany ..................... 210/629 |
| 5,948,262 A | 9/1999 | Todd et al. .................. 210/616 |
| 5,962,309 A * | 10/1999 | Kumagai et al. ............ 210/617 |
| 5,980,738 A | 11/1999 | Heitkamp et al. .......... 210/150 |
| 5,981,272 A | 11/1999 | Chang ..................... 435/299.1 |
| 5,985,148 A | 11/1999 | Liu .............................. 210/605 |
| 5,993,650 A | 11/1999 | Kim ............................ 210/150 |
| 6,015,497 A * | 1/2000 | Steen, Jr. ..................... 210/150 |
| 6,063,268 A | 5/2000 | Jowett ......................... 210/150 |
| 6,077,424 A | 6/2000 | Karsukura et al. .......... 210/616 |
| 6,126,829 A | 10/2000 | Gunnarsson et al. ........ 210/616 |
| 6,136,194 A | 10/2000 | Vogel et al. ................. 210/150 |
| 6,156,204 A | 12/2000 | Todd et al. .................. 210/616 |
| 6,210,578 B1 | 4/2001 | Sagastume et al. ......... 210/151 |

* cited by examiner

Primary Examiner—Christopher Upton
(74) Attorney, Agent, or Firm—Darby & Darby

(57) ABSTRACT

A biofilm support including a plastic biofilm support element having a maximum dimension which does not exceed 50 mm and having a specific gravity of between approximately 0.70–0.91. A method of manufacture of a biofilm support and a waste water treatment system employing the biofilm support are also disclosed.

53 Claims, 4 Drawing Sheets

BIOFILM CARRIER, METHOD OF MANUFACTURE THEREOF AND WASTE WATER TREATMENT SYSTEM EMPLOYING BIOFILM CARRIER

FIELD OF THE INVENTION

The present invention relates to waste water treatment generally and more particularly to the use of biofilm supports.

BACKGROUND OF THE INVENTION

The following U.S. Pat. Nos. are believed to represent the current state of the art: U.S. Pat. Nos. 5,980,738; 5,981,272; 5,985,148; 5,993,650; 6,063,268; 6,156,204; 5,948,262; 5,871,674; 5,783,066; 5,783,069; 6,126,829; 5,543,039; 5,458,779; 5,486,292; 4,985,182; 4,333,893; 5,217,616; 4,814,085; 4,814,125; 4,842,920; 5,168,058; 4,385,988; 4,522,767; 4,537,731.

SUMMARY OF THE INVENTION

The present invention seeks to provide an improved biofilm support as well as an improved waste water treatment system and methodology using the biofilm support.

There is thus provided, in accordance with a preferred embodiment of the present invention, a biofilm support, including a plastic biofilm support element having a maximum dimension which does not exceed 50 mm and having a specific gravity of between approximately 0.70–0.91.

There is additionally provided, in accordance with a preferred embodiment of the present invention, a biofilm support, including a plastic biofilm support element having a generally cylindrical configuration and including a plurality of radially extending surfaces extending outwardly from a generally solid center.

There is further provided, in accordance with a preferred embodiment of the present invention, a biofilm support, including a unitary plastic biofilm support element having a maximum dimension which does not exceed 50 mm and includes a plurality of roughened biofilm adherence surfaces integrally formed as one piece therewith.

There is still further provided, in accordance with a preferred embodiment of the present invention, a waste water treatment system, including a basin, at least one airlift operating in the basin and a multiplicity of plastic biofilm support elements, having any of the above characteristics, disposed in the basin for cooperation with the airlift.

There is yet further provided, in accordance with a preferred embodiment of the present invention, a method of manufacturing a plastic biofilm support element including:

extruding a plastic material mixed with a foaming agent to produce an elongate extruded plastic material having a specific gravity of between approximately 0.70–0.91;

cooling the elongate extruded plastic material; and cutting the elongate extruded plastic material to have a maximum dimension which does not exceed 50 mm.

There is additionally provided, in accordance with a preferred embodiment of the present invention, a method of manufacturing a plastic biofilm support element including:

extruding a plastic material mixed with a foaming agent to produce an elongate extruded plastic material having a generally cylindrical configuration and including a plurality of radially extending surfaces extending outwardly from a generally solid center;

cooling the elongate extruded plastic material; and cutting the elongate extruded plastic material to have a maximum dimension which does not exceed 50 mm.

There is yet additionally provided, in accordance with a preferred embodiment of the present invention, a method of manufacturing a plastic biofilm support element including:

extruding a plastic material mixed with a foaming agent to produce an elongate extruded plastic material having a plurality of roughened biofilm adherence surfaces integrally formed as one piece therewith;

cooling the elongate extruded plastic material; and cutting the elongate extruded plastic material to have a maximum dimension which does not exceed 50 mm.

Preferably, the plastic biofilm support element has a generally cylindrical configuration and includes a plurality of radially extending surfaces extending outwardly from a generally solid center.

In accordance with a preferred embodiment of the present invention, the plastic biofilm support element has a plurality of roughened biofilm adherence surfaces integrally formed as one piece therewith.

Preferably, the plurality of radially extending ribs includes between 5 and 9 ribs.

In accordance with a preferred embodiment of the present invention, each of the plurality of ribs has a thickness of between 0.5 and 2 mm.

Preferably, the plastic biofilm support element includes a strip extending along an outwardly facing edge of each of the radially extending ribs.

In accordance with a preferred embodiment of the present invention, the plastic biofilm support element is formed of a plastic material selected from the following plastic materials: polyolefin, polystyrene, polyvinyl chloride and polyurethane.

Preferably, the plastic biofilm support element is formed of a plastic material mixed with a foaming agent.

In accordance with a preferred embodiment of the present invention, the plurality of ribs and the strips are configured so as to prevent interdigitation between ribs of two separate biofilm support elements.

Preferably, the support is configured so as to prevent mechanically retained joining of two separate biofilm support elements.

Preferably, the plastic biofilm support element has a specific gravity of between approximately 0.75–0.89 and more preferably between approximately 0.81–0.87.

In accordance with a preferred embodiment of the present invention, the roughened biofilm adherence surfaces have a roughness average (Ra) in the range of 100–800 microns and more preferably in the range of 200–500 microns.

Preferably, the plurality of radially extending surfaces are defined by a plurality of radially extending ribs.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1A:
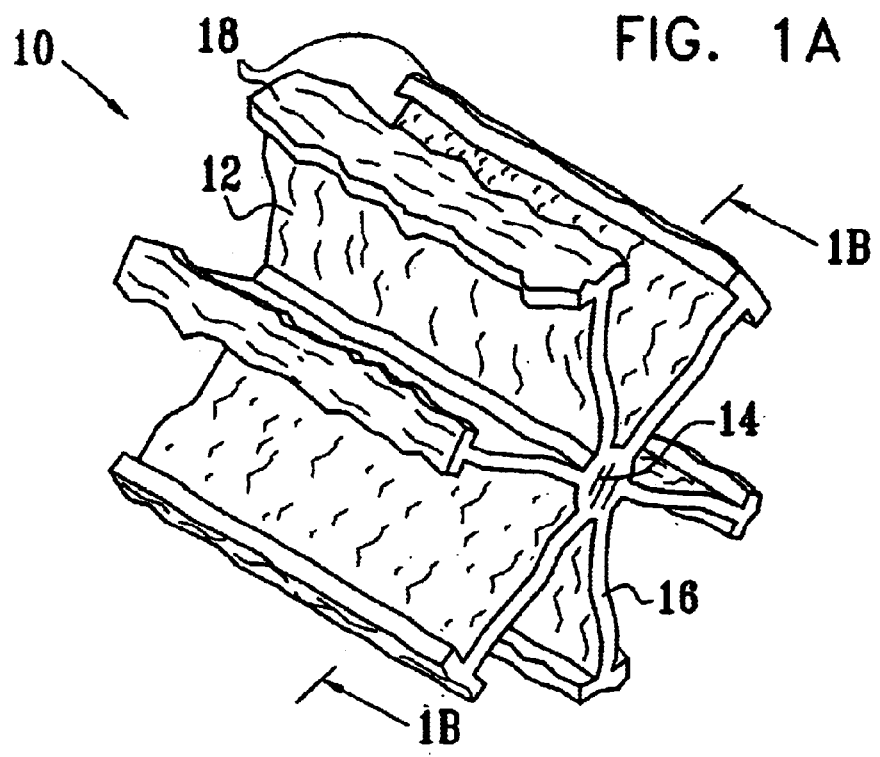
FIGS. 1A and 1B are respective simplified pictorial and sectional illustrations of a biofilm support constructed and operative in accordance with a preferred embodiment of the present invention.
Figure 1B:
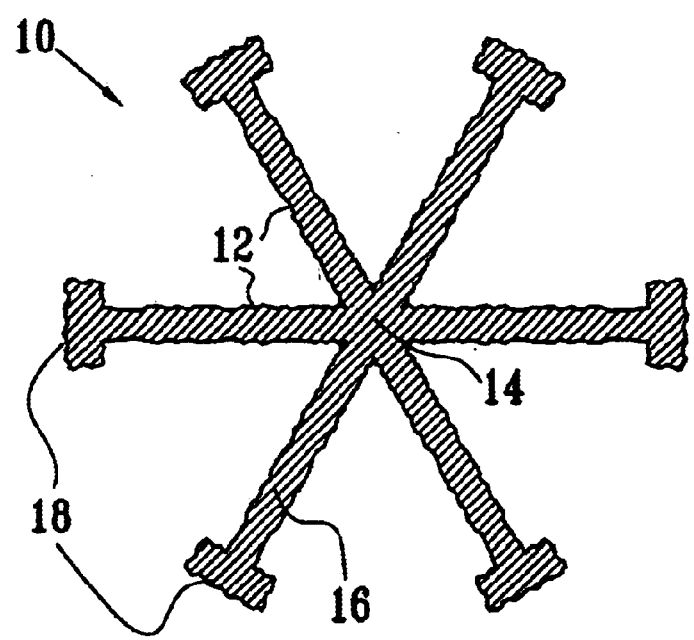

Reference is now made to FIGS. 1A and 1B, which are respective simplified pictorial and sectional illustrations of a biofilm support constructed and operative in accordance with a preferred embodiment of the present invention. As seen in FIGS. 1A and 1B, there is provided a biofilm support element 10 formed of plastic, having a maximum dimension which does not exceed 50 mm and having a specific gravity of between approximately 0.70–0.91.

Preferably, biofilm support element 10 has a generally cylindrical configuration and includes a plurality of radially extending surfaces 12 extending outwardly from a generally solid center 14. In accordance with a preferred embodiment of the present invention surfaces 12 are integrally formed as one piece with the solid center 14, preferably by extrusion, and define opposite side surfaces of a plurality of radially extending ribs 16, preferably between five and nine in number. In accordance with a preferred embodiment of the present invention, each of ribs 16 has a thickness of between 0.5 and 2 mm.

In accordance with a preferred embodiment of the present invention, a transverse strip 18 is provided along an outwardly facing edge of each rib 16. Additional transverse strips may also be provided along each rib. In the embodiment of FIGS. 1A and 1B, the width of each strip is preferably equal to approximately 15–60 percent, and more preferably equal to approximately 20–40 percent, of the overall circumference of the cylindrical biofilm support element 10, divided by the number of ribs 16.

It is a particular feature of the present invention that the biofilm support element 10 and specifically ribs 16 and strips 18 are configured so as to prevent retained interdigitation between ribs of two separate biofilm support elements. In the embodiment of FIGS. 1A and 1B, interdigitation can occur, but upon such interdigitation, two separate biofilm support elements readily disengage. Accordingly, the biofilm support element 10 of FIGS. 1A and 1B is preferably configured so as to prevent mechanically retained joining of two separate biofilm support elements 10.

In accordance with a preferred embodiment of the present invention, biofilm support element 10 is formed of a plastic material selected from the following plastic materials: polyolefin, polystyrene, polyvinyl chloride and polyurethane. Polypropylene having a melt flow index typically in the range of 0.5–10 is the preferred material.

In accordance with a preferred embodiment of the present invention, biofilm support element 10 has a specific gravity of between approximately 0.75–0.89 and most preferably between approximately 0.81–0.87.

It is a particular feature of the invention that the surfaces 12 of ribs 16, as well as all other exposed surfaces of biofilm support element 10, are roughened. Preferably, some or all of the roughened biofilm adherence surfaces have a roughness average (Ra) in the range of 100–800 microns and most preferably in the range of 200–500 microns.

Figure 2A:
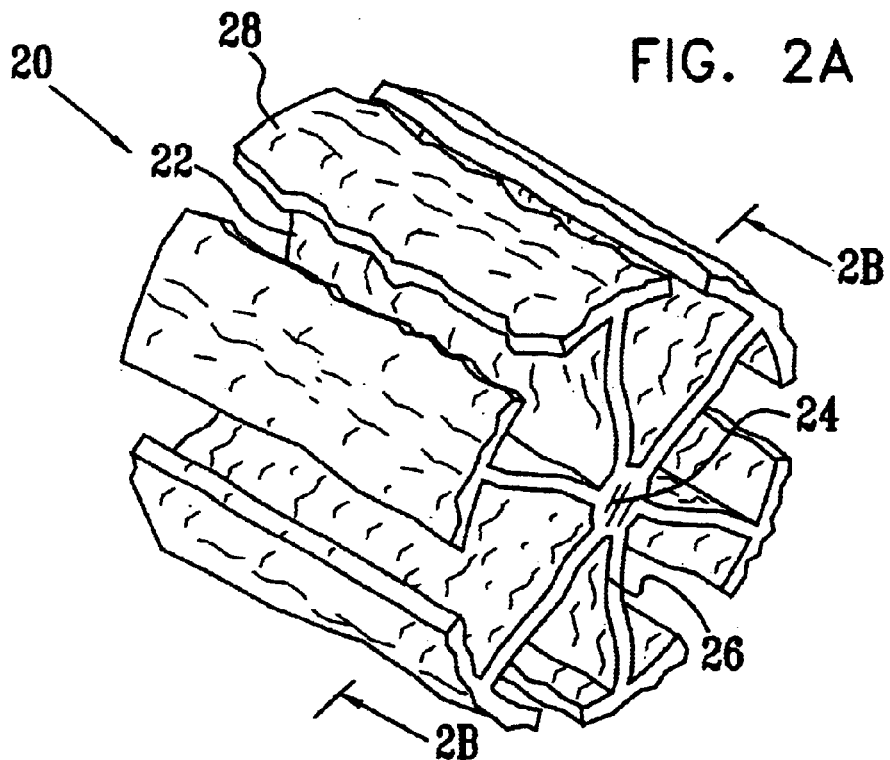
FIGS. 2A and 2B are respective simplified pictorial and sectional illustrations of a biofilm support constructed and operative in accordance with another preferred embodiment of the present invention.
Figure 2B:
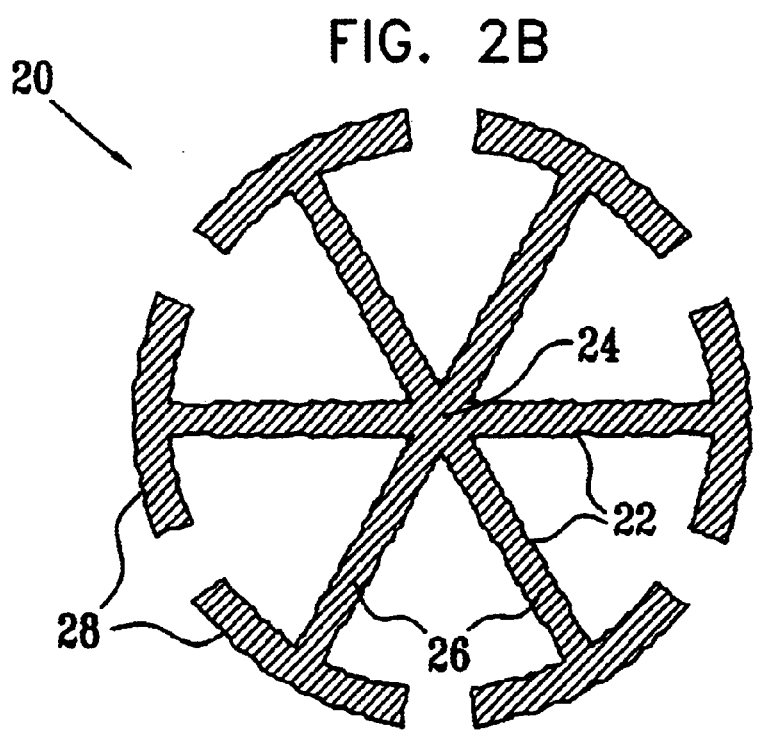

Reference is now made to FIGS. 2A and 2B, which are respective simplified pictorial and sectional illustrations of a biofilm support constructed and operative in accordance with a preferred embodiment of the present invention. As seen in FIGS. 2A and 2B, there is provided a biofilm support element 20, similar to that of FIGS. 1A and 1B, formed of plastic, having a maximum dimension which does not exceed 50 mm and having a specific gravity of between approximately 0.70–0.91.

Preferably and similarly to biofilm support element 10 (FIGS. 1A & 1B), biofilm support element 20 has a generally cylindrical configuration and includes a plurality of radially extending surfaces 22 extending outwardly from a generally solid center 24. In accordance with a preferred embodiment of the present invention, surfaces 22 are integrally formed as one piece with the solid center 24, preferably by extrusion, and define opposite side surfaces of a plurality of radially extending ribs 26, preferably between five and nine in number. In accordance with a preferred embodiment of the present invention, each of ribs 26 has a thickness of between 0.5 and 2 mm.

In accordance with a preferred embodiment of the present invention, a transverse strip 28 is provided along an outwardly facing edge of each rib 26. Additional transverse strips may also be provided along each rib. In the embodiment of FIGS. 2A and 2B, the width of each strip is preferably equal to approximately 60–90 percent of the overall circumference of the cylindrical biofilm support element 20, divided by the number of ribs 26.

It is a particular feature of the present invention that the biofilm support element 20 and specifically ribs 26 and strips 28 are configured so as to prevent interdigitation between ribs of two separate biofilm support elements. In the embodiment of FIGS. 2A and 2B, interdigitation cannot occur. Accordingly, the biofilm support element 20 of FIGS. 2A and 2B is preferably configured so as to prevent mechanically retained joining of two separate biofilm support elements 20.

In accordance with a preferred embodiment of the present invention, similarly to biofilm support element 10 (FIGS. 1A & 1B), biofilm support element 20 is formed of a plastic material selected from the following plastic materials: polyolefin, polystyrene, polyvinyl chloride and polyurethane. Polypropylene having a melt flow index typically in the range of 0.5–10 is the preferred material.

In accordance with a preferred embodiment of the present invention, biofilm support element 20 has a specific gravity of between approximately 0.75–0.89 and most preferably between approximately 0.81–0.87.

It is a particular feature of the invention that the surfaces 22 of ribs 26, as well as other exposed surfaces of biofilm support element 20, are roughened. Preferably, some or all of the roughened biofilm adherence surfaces have a roughness average (Ra) in the range of 100–800 microns and most preferably in the range of 200–500 microns.

Figure 3:
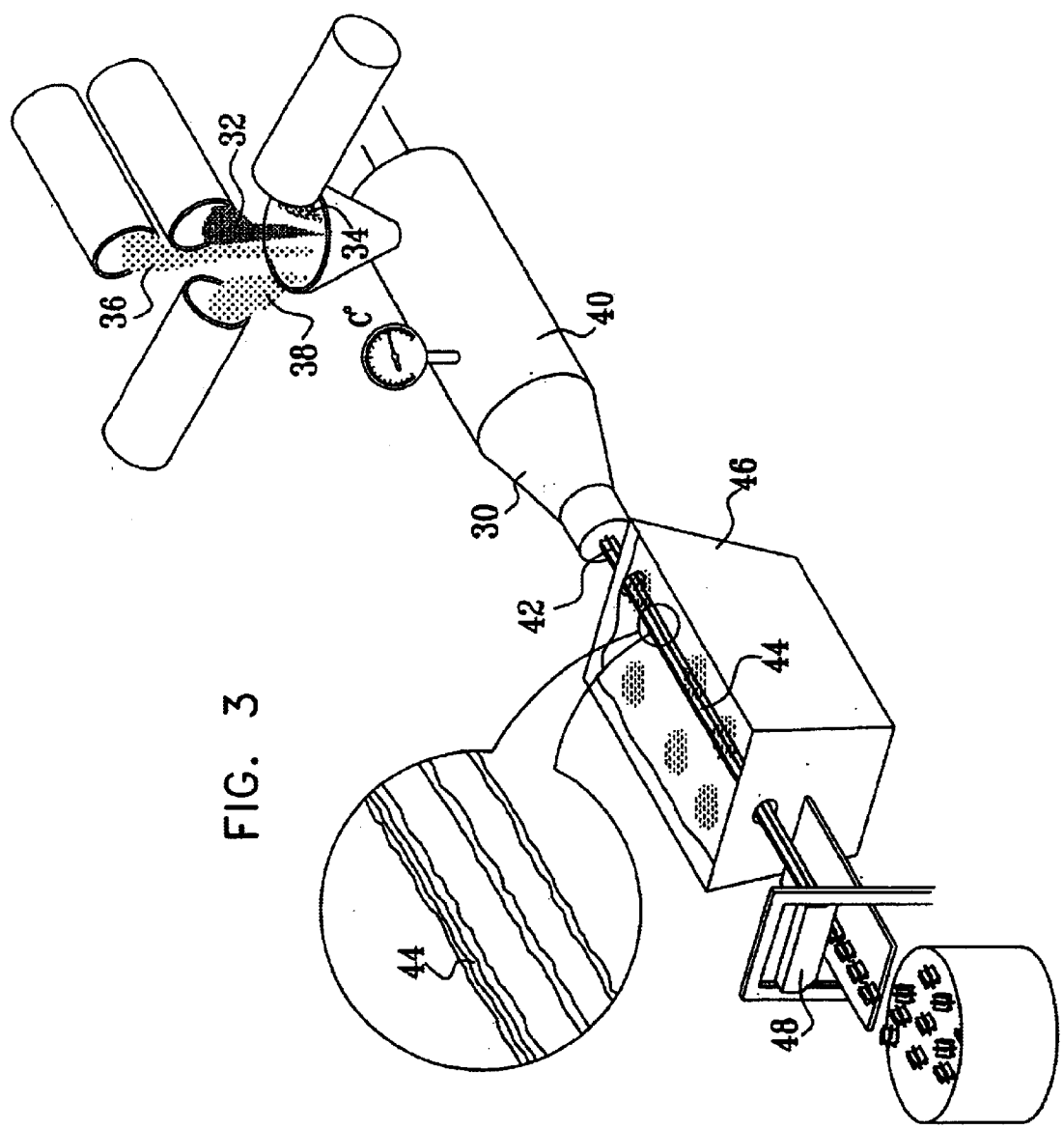
FIG. 3 is a simplified illustration of a methodology for forming a biofilm support in accordance with a preferred embodiment of the present invention.

Reference is now made to FIG. 3, which is a simplified illustration of a methodology for forming a biofilm support in accordance with a preferred embodiment of the present invention. As seen in FIG. 3 an extruder 30, which may be a conventional extruder, receives a mixture of materials, preferably including a plastic material 32 selected from the following plastic materials: polyolefin, polystyrene, polyvinyl chloride and polyurethane. Polypropylene having a melt flow index typically in the range of 0.5–10 is the preferred material.

In accordance with a preferred embodiment of the invention, one or more foaming agents, and preferably the following foaming agents, are supplied to the extruder together with the plastic material:

an exothermic foaming agent 34, preferably azodicarbon amide; and an endothermic foaming agent 36, preferably sodium bicarbonate or a derivative thereof.

Additionally in accordance with a preferred embodiment of the present agent, a filler 38, preferably limestone or talc, is also added.

Preferred proportions of the foregoing constituents by weight, for each one unit of plastic by weight, are as follows:

exothermic foaming agent 34—0–2%
endothermic foaming agent 36—0–3%
filler 38—0–10%

Most preferred proportions of the foregoing constituents by weight, for each one unit of polypropylene by weight, are as follows:

exothermic foaming agent 34—0.3–1.5%
endothermic foaming agent 36—1–2.5%
filler 38—0–5%

The foregoing constituents are preferably premixed together prior to being supplied to the extruder 30 and are preferably supplied in a granulated form.

The extruder 30 is preferably operated so as to have a bell shaped temperature profile along a longitudinal axis 40, such that the highest temperature in the extruder 30 is at a location intermediate the flowpath of material therethrough.

The extruder 30 is preferably formed with a nozzle 42, across which there is provided a pressure drop of at least 1500 psi.

A roughened extruded elongate profile 44 exits nozzle 42 into a cooling bath 46. The profile 44 is drawn by a puller (not shown) and is cut into appropriate lengths by a cutter 48.

Figure 4:
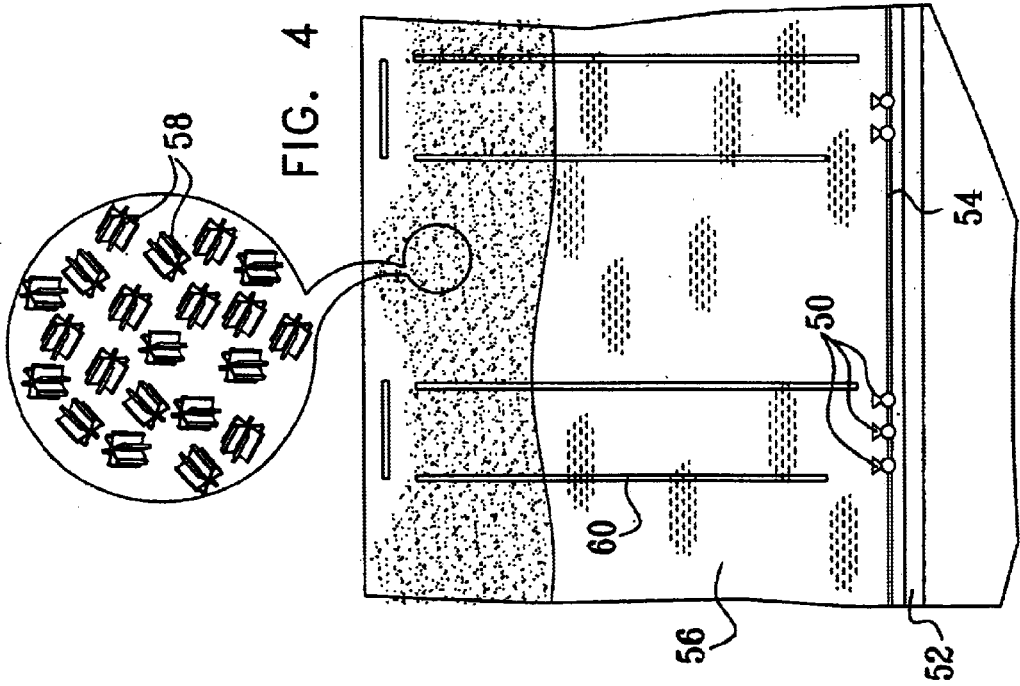
FIGS. 4 and 5 are simplified illustrations of a portion of a waste water treatment system and methodology employing a biofilm support in accordance with a preferred embodiment of the present invention.
Figure 5:
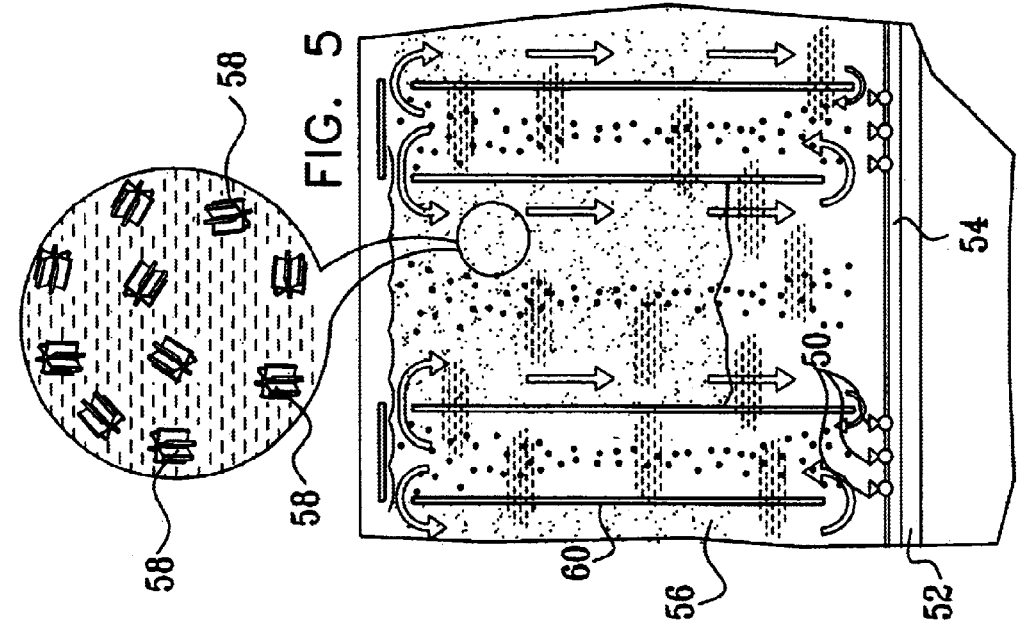

Reference is now made to FIGS. 4 and 5, which are simplified illustrations of a waste water treatment system and methodology employing a biofilm support in accordance with a preferred embodiment of the present invention. As seen in FIGS. 4 and 5, biofilm support element 10 (FIGS. 1A and 1B) or biofilm support element 20 (FIGS. 2A and 2B) may be advantageously employed in an air-lift type waste water treatment system and methodology. A preferred such system is described in applicants' co-pending U.S. patent application Ser. No. 09/866,886, filed May 29, 2001, entitled METHOD AND APPARATUS FOR BIOLOGICAL WASTEWATER TREATMENT, the disclosure of which is hereby incorporated by reference.

As seen in FIG. 4, an air-lift waste water treatment system and methodology employs a pressurized air supply, typically including nozzles 50, located near the floor of a basin 52, which are supplied with pressurized air from a compressor (not shown) via pipes 54. Waste water 56 fills part of basin 52, and a multiplicity of biofilm supports 58, such as biofilm support element 10 (FIGS. 1A & 1B) or 20 (FIGS. 2A & 2B) described hereinabove, float at the top of the waste water 56, as shown. Preferably, generally cylindrical upstanding air lift enclosures 60 are provided overlying nozzles 50.

As seen in FIGS. 4 and 5, the air-lift waste water treatment system and methodology employs pressurized air from nozzles 50 to cause an upward flow of waste water 56 through air lift enclosures 60. This causes biofilm supports 58 to be inversely fluidized in waste water 56, thereby providing enhanced turbulence and mass transfer for efficient waste water treatment.

It will be appreciated by persons skilled in the art that the present invention is not limited by what has been particularly shown and described hereinabove. Rather the scope of the present invention includes both combinations and subcombinations of the various features described hereinabove as well as variations and modifications which would occur to persons skilled in the art upon reading the specification and which are not in the prior art.

We claim:

1. A waste water treatment system comprising:
   a basin;
   at least one airlift, operating in said basin, comprising a series of airlifts including:
      an initial air lift assembly including an upstream partition which extends downwardly from a top location above a water level in said basin to a bottom location spaced from a bottom of said basin; and
      at least one intermediate air lift assembly; and
   a multiplicity of plastic biofilm support elements disposed in said basin for cooperation with said at least one airlift, said plastic biofilm support elements having a maximum dimension which does not exceed 50 mm and having a specific gravity of between approximately 0.70–0.91,
   whereby supplying waste water from an upstream side of said basin, by providing a flow of water from a waste water inlet to a treated water outlet and allowing said waste water, but generally not said support elements, to flow from said water inlet to said water outlet and operating said at least one airlift provides aerobic waste water flow therein in operative engagement with said support elements,
   wherein said flow is an undulating flow and includes passage under said upstream partition which is of relatively low volume and generally does not carry said support elements into said series of air lifts, thereby constraining said particles to reside outside of and between said series of air lifts.

2. A waste water treatment system according to claim 1 and wherein said plastic biofilm support elements have a generally cylindrical configuration and include a plurality of radially extending surfaces extending outwardly from a generally solid center.

3. A waste water treatment system according to claim 2 and wherein said plastic biofilm support elements have a plurality of roughened biofilm adherence surfaces integrally formed as one piece therewith.

4. A waste water treatment system according to claim 3 and wherein said plurality of radially extending surfaces are defined by a plurality of radially extending ribs.

5. A waste water treatment system according to claim 4 and wherein said plurality of radially extending ribs comprises between 5 and 9 ribs.

6. A waste water treatment system according to claim 4 and wherein each of said plurality of ribs has a thickness of between 0.5 and 2 mm.

7. A waste water treatment system according to claim 4 and wherein said plastic biofilm support elements include a strip extending along an outwardly facing edge of each of said radially extending ribs.

8. A waste water treatment system according to claim 7 and wherein said plurality of ribs and said strips are configured so as to prevent interdigitation between ribs of two separate biofilm support elements.

9. A waste water treatment system according to claim 3 and wherein said plastic biofilm support elements are formed of a plastic material selected from the following plastic materials: polyolefin, polystyrene, polyvinyl chloride and polyurethane.

10. A waste water treatment system according to claim 3 and wherein said plastic biofilm support elements are formed of a plastic material mixed with a foaming agent.

11. A waste water treatment system according to claim 3 and being configured so as to prevent mechanically retained joining of two separate biofilm support elements.

12. A waste water treatment system according to claim 11 and wherein said plurality of radially extending surfaces are defined by a plurality of radially extending ribs.

13. A waste water treatment system according to claim 12 and wherein said plurality of radially extending ribs comprises between 5 and 9 ribs.

14. A waste water treatment system according to claim 3 and wherein said plastic biofilm support elements have a specific gravity of between approximately 0.75–0.89.

15. A waste water treatment system according to claim 3 and wherein said plastic biofilm support elements have a specific gravity of between approximately 0.81–0.87.

16. A waste water treatment system according to claim 3 and wherein said roughened biofilm adherence surfaces have a roughness average (Ra) in the range of 100–800 microns.

17. A waste water treatment system according to claim 3 and wherein said roughened biofilm adherence surfaces have a roughness average (Ra) in the range of 200–500 microns.

18. A waste water treatment system according to claim 2 and wherein said plurality of radially extending surfaces are defined by a plurality of radially extending ribs.

19. A waste water treatment system according to claim 18 and wherein said plurality of radially extending ribs comprises between 5 and 9 ribs.

20. A waste water treatment system according to claim 18 and wherein each of said plurality of ribs has a thickness of between 0.5 and 2 mm.

21. A waste water treatment system according to claim 18 and wherein said plastic biofilm support elements include a strip extending along an outwardly facing edge of each of said radially extending ribs.

22. A waste water treatment system according to claim 21 and wherein said plurality of ribs and said strips are configured so as to prevent interdigitation between ribs of two separate biofilm support elements.

23. A waste water treatment system according to claim 1 and wherein said plastic biofilm support elements have a plurality of roughened biofilm adherence surfaces integrally formed as one piece therewith.

24. A waste water treatment system according to claim 23 and wherein said roughened biofilm adherence surfaces have a roughness average (Ra) in the range of 100–800 microns.

25. A waste water treatment system according to claim 23 and wherein said roughened biofilm adherence surfaces have a roughness average (Ra) in the range of 200–500 microns.

26. A waste water treatment system according to claim 1 and wherein said plastic biofilm support elements are formed of a plastic material selected from the following plastic materials: polyolefin, polystyrene, polyvinyl chloride and polyurethane.

27. A waste water treatment system according to claim 1 and wherein said plastic biofilm support elements are formed of a plastic material mixed with a foaming agent.

28. A waste water treatment system according to claim 1 and being configured so as to prevent mechanically retained joining of two separate biofilm support elements.

29. A waste water treatment system according to claim 1 and wherein said plastic biofilm support elements have a specific gravity of between approximately 0.75–0.89.

30. A waste water treatment system according to claim 1 and wherein said plastic biofilm support elements have a specific gravity of between approximately 0.81–0.87.

31. A waste water treatment system comprising:
a basin;
at least one airlift, operating in said basin, comprising a series of airlifts including:
an initial air lift assembly including an upstream partition which extends downwardly from a top location above a water level in said basin to a bottom location spaced from a bottom of said basin; and
at least one intermediate air lift assembly; and
a multiplicity of plastic biofilm support elements disposed in said basin for cooperation with said at least one airlift, said plastic biofilm support elements having a generally cylindrical configuration and including a plurality of radially extending surfaces extending outwardly from a generally solid center,
whereby supplying waste water from an upstream side of said basin, by providing a flow of water from a waste water inlet to a treated water outlet and allowing said waste water, but generally not said support elements, to flow from said water inlet to said water outlet and operating said at least one airlift provides aerobic waste water flow therein in operative engagement with said support elements,
wherein said flow is an undulating flow and includes passage under said upstream partition which is of relatively low volume and generally does not carry said support elements into said series of air lifts, thereby constraining said particles to reside outside of and between said series of air lifts.

32. A waste water treatment system according to claim 31 and wherein said plastic biofilm support elements have a plurality of roughened biofilm adherence surfaces integrally formed as one piece therewith.

33. A waste water treatment system according to claim 32 and wherein said roughened biofilm adherence surfaces have a roughness average (Ra) in the range of 100–800 microns.

34. A waste water treatment system according to claim 32 and wherein said roughened biofilm adherence surfaces have a roughness average (Ra) in the range of 200–500 microns.

35. A waste water treatment system according to claim 31 and wherein said plurality of radially extending surfaces are defined by a plurality of radially extending ribs.

36. A waste water treatment system according to claim 35 and wherein said plurality of radially extending ribs comprises between 5 and 9 ribs.

37. A waste water treatment system according to claim 35 and wherein each of said plurality of ribs has a thickness of between 0.5 and 2 mm.

38. A waste water treatment system according to claim 35 and wherein said plastic biofilm support elements include a strip extending along an outwardly facing edge of each of said radially extending ribs.

39. A waste water treatment system according to claim 38 and wherein said plurality of ribs and said strips are configured so as to prevent interdigitation between ribs of two separate biofilm support elements.

40. A waste water treatment system according to claim 31 and wherein said plastic biofilm support elements are formed of a plastic material selected from the following plastic materials: polyolefin, polystyrene, polyvinyl chloride and polyurethane.

41. A waste water treatment system according to claim 31 and wherein said plastic biofilm support elements are formed of a plastic material mixed with a foaming agent.

42. A waste water treatment system according to claim 31 and being configured so as to prevent mechanically retained joining of two separate biofilm support elements.

43. A waste water treatment system comprising:

a basin;

at least one airlift, operating in said basis, comprising a series of airlifts including:
- an initial air lift assembly including an upstream partition which extends downwardly from a top location above a water level in said basin to a bottom location spaced from a bottom of said basin; and
- at least one intermediate air lift assembly; and a multiplicity of plastic biofilm support elements disposed in said basin for cooperation with said at least one airlift, said plastic biofilm support elements having a maximum dimension which does not exceed 50 mm and including a plurality of roughened biofilm adherence surfaces integrally formed as one piece therewith, whereby supplying waste water from an upstream side of said basin, by providing a flow of water from a waste water inlet to a treated water outlet and allowing said waste water, but generally not said support elements, to flow from said water inlet to said water outlet and operating said at least one airlift provides aerobic waste water flow therein in operative engagement with said support elements, wherein said flow is an undulating flow and includes passage under said upstream partition which is of relatively low volume and generally does not carry said support elements into said series of air lifts, thereby constraining said particles to reside outside of and between said series of air lifts.

44. A waste water treatment system according to claim 43 and wherein said biofilm support elements include a plurality of radially extending surfaces defined by a plurality of radially extending ribs.

45. A waste water treatment system according to claim 44 and wherein said plurality of radially extending ribs comprises between 5 and 9 ribs.

46. A waste water treatment system according to claim 44 and wherein each of said plurality of ribs has a thickness of between 0.5 and 2 mm.

47. A waste water treatment system according to claim 44 and wherein said plastic biofilm support elements include a strip extending along an outwardly facing edge of each of said radially extending ribs.

48. A waste water treatment system according to claim 47 and wherein said plurality of ribs and said strips are configured so as to prevent interdigitation between ribs of two separate biofilm support elements.

49. A waste water treatment system according to claim 43 and wherein said plastic biofilm support elements are formed of a plastic material selected from the following plastic materials: polyolefin, polystyrene, polyvinyl chloride and polyurethane.

50. A waste water treatment system according to claim 43 and wherein said plastic biofilm support elements are formed of a plastic material mixed with a foaming agent.

51. A waste water treatment system according to claim 43 and being configured so as to prevent mechanically retained joining of two separate biofilm support elements.

52. A waste water treatment system according to claim 43 and wherein said roughened biofilm adherence surfaces have a roughness average (Ra) in the range of 100–800 microns.

53. A waste water treatment system according to claim 43 and wherein said roughened biofilm adherence surfaces have a roughness average (Ra) in the range of 200–500 microns.

* * * * *

UNITED STATES PATENT AND TRADEMARK OFFICE
CERTIFICATE OF CORRECTION

PATENT NO. : 6,726,838 B2
DATED : April 27, 2004
INVENTOR(S) : Ronen I. Shechter et al.

It is certified that error appears in the above-identified patent and that said Letters Patent is hereby corrected as shown below:

<u>Title page,</u>
Item [73], Assignee, delete "Agwise Wise Water Technologies Ltd." and substitute with -- Aqwise Wise Water Technologies Ltd. --.

Signed and Sealed this

Ninth Day of November, 2004

JON W. DUDAS
*Director of the United States Patent and Trademark Office*